United States Patent [19]
Ferhut et al.

[11] Patent Number: 5,948,420
[45] Date of Patent: Sep. 7, 1999

[54] PHARMACEUTICAL AND COSMETIC COMPOSITIONS AND THEIR PRODUCTION

[75] Inventors: Faridoon Ferhut, Virginia Beach, Va.; Diana Smith, Burlington County, N.J.

[73] Assignee: Ciba Specialty Chemicals Water Treatments Limited, West Yorkshire, United Kingdom

[21] Appl. No.: 09/069,973

[22] Filed: Apr. 30, 1998

Related U.S. Application Data

[60] Provisional application No. 60/044,443, Apr. 30, 1997.

[51] Int. Cl.$^6$ ............................ A61K 7/075; A61K 7/48; A61K 9/10; A61K 47/14
[52] U.S. Cl. .................. 424/401; 252/315.1; 252/315.4; 424/486; 424/487; 424/70.11; 424/70.16; 424/70.17; 514/772; 514/788; 514/944
[58] Field of Search .................................... 424/401, 486, 424/487, 70.11, 70.16, 70.17; 252/315.1, 315.4; 514/772, 788, 944

[56] References Cited

U.S. PATENT DOCUMENTS

| | | | |
|---|---|---|---|
| 4,950,475 | 8/1990 | Vishnupad et al. | 424/83 |
| 4,954,336 | 9/1990 | Janchipraponvej | 424/70 |
| 5,275,809 | 1/1994 | Chen et al. | 424/70 |
| 5,296,218 | 3/1994 | Chen et al. | 424/70 |
| 5,358,667 | 10/1994 | Bergmann | 252/547 |
| 5,609,862 | 3/1997 | Chen et al. | 424/70.11 |
| 5,631,000 | 5/1997 | Pellico et al. | 424/53 |
| 5,766,613 | 6/1998 | Arraudeau et al. | 424/401 |
| 5,827,508 | 10/1998 | Tanner et al. | 424/59 |

*Primary Examiner*—Jeffrey E. Russel
*Attorney, Agent, or Firm*—David R. Crichton

[57] ABSTRACT

Substantially clear gelled compositions suitable for use in cosmetics or pharmaceutical compositions and containing cationic polymer are formed by solvating a reverse phase emulsion of water soluble or water swellable cationic polymer in a liquid hydrophobic ester of a polyol with a polyol mixture which contains propylene glycol and/or butylene glycol together with glycerine in proportions which result in a composition having a clarity of below 30 NTU.

10 Claims, No Drawings

PHARMACEUTICAL AND COSMETIC COMPOSITIONS AND THEIR PRODUCTION

CROSS REFERENCE TO RELATED APPLICATION

This application is an application filed under 35 U.S.C. §111(a) claiming benefit pursuant to 35 U.S.C. §119(e)(1) of the filing date of the Provisional Application 60/044,443, filed Apr. 30, 1997, pursuant to 35 U.S.C. §111(b).

FIELD OF THE INVENTION

This invention relates to starter compositions which can be used as the basis of pharmaceutical or cosmetic compositions, and to the pharmaceutical or cosmetic compositions themselves. It also relates to the production of such compositions.

It is common practice to formulate a pharmaceutical or cosmetic composition as a gel which can have moderate or high viscosity. This is normally achieved by incorporation of appropriate polymeric thickeners and solvents or diluents. Often the final gelled composition is made by formulating a gelled starter composition from the polymer and solvents, and incorporating active ingredients and minor additives into the starter composition. Although a few of the starter and final compositions are clear, the majority are either cloudy or, more usually, very opaque.

By referring to a gel, or a gelled composition, we mean a shear thinning composition which is highly viscous, at rest and which has lower viscosity under shear, e.g., being a paste or being relatively fluid such as cream. Petrolatum jelly is an example of a gelled composition.

One very valuable range of pharmaceutical and cosmetic compositions is made by using as the polymer a cationic polymer formed from water soluble ethylenically unsaturated monomer or monomer blend and which is provided to the formulator of the composition as a reverse phase emulsion in a liquid hydrophobic ester, ie an ester which has sufficiently low miscibility with water that it can be used as the non-aqueous phase in a reverse phase polymerisation ester. The liquid ester must have substantially no solvating effect for the polymer, or for the monomers from which it is formed, throughout the range of temperatures at which the polymer is likely to be formed (for instance 15 to 100° C.), since if the liquid ester does have any significant solvating effect for the polymer the liquid ester would then be an unsatisfactory medium for the reverse phase emulsion polymerisation. However it is necessary to solvate the polymer in the composition in order that the polymer particles dissolve or swell to the extent necessary to give the desired optimum viscosity and gel characteristics to the composition. In order to achieve this solvation, it is necessary to add a polar liquid.

With all known compositions, the known combinations of polymer, ester of polyol and solvating polar liquid have resulted in the composition having the same opaque or cloudy appearance which is typical of most gelled compositions.

It would be desirable to be able to provide a clear gelled composition based on a blend of water soluble or water swellable cationic polymer and a liquid ester of a polyol.

SUMMARY OF THE INVENTION

A clear gelled composition according to the invention comprises (a) 0.5 to 5% of a water soluble or water swellable cationic polymer formed from water soluble ethylenically unsaturated monomer or monomer blend, (b) 0.5 to 5% of a hydrophobic ester wherein the amount of the ester is 0.5 to 2 parts by weight per part by weight of the cationic polymer and the ester is a liquid which is substantially non-solvating for the polymer throughout the range 15 to 100° C., and (c) 80 to 97% of a polyol mixture which solvates the polymer into a viscous gel and which comprises (c1) 30 to 88% of propylene glycol and/or butylene glycol, (c2) 8 to 55% of glycerine and (c3) 0 to 35% of other polyol, and wherein the amounts of c1, c2 and c3 are selected such that the composition has a clarity of below 30 NTU.

All percentages are by weight based on the total weight of composition, unless otherwise specified.

The term "polyol" is intended to include dihydroxy compounds as well as compounds having higher numbers of hydroxy groups, as explained below.

The clarity values are determined by a Hach procedure, as described below.

The invention also provides a method of making a clear viscous composition, wherein the method comprises providing a substantially anhydrous reverse phase emulsion of water soluble or water swellable cationic polymer formed of water soluble ethylenically unsaturated monomer or monomer blend suspended in 0.5 to 2 parts by weight (per part by weight polymer) of a liquid hydrophobic ester wherein the liquid ester is substantially non-solvating for the polymer throughout the range 15 to 100° C., and blending 1 to 10% of the reverse phase emulsion with 50 to 97% of a polyol mixture which solvates the polymer into a gel and which comprises 30 to 88% of propylene glycol and/or butylene glycol, 8 to 55% of glycerine, and 0 to 35% of other polyol, wherein the amounts of these components are selected such that the composition has a clarity of below 30 ntu.

DESCRIPTION OF THE PREFERRED EMBODIMENTS

The cationic polymer is formed from water soluble ethylenically unsaturated monomer or monomer blend. It may be formed from a single monomer which is cationic or it may be formed from a blend of cationic monomers or a blend of cationic monomer with a non-ionic or, in some instances, a minor amount of anionic monomer. The blend must be water soluble to enable reverse phase polymerisation to be formed.

Water soluble non-ionic monomers include materials such as vinyl pyrollidone, hydroxy ethyl acrylate or other hydroxy substituted acrylic or methacrylic ester which is water soluble, or acrylamide. Anionic monomers include carboxylic monomers such as acrylic acid or methacrylic acid or sulphonic polymers. If a blend is used, the amount of cationic monomer is preferably more than 50% by weight of the blend, and usually it is at least 70% or at least 80% by weight of the blend. The preferred polymers are formed wholly of cationic monomer.

The cationic monomer can be a diallyl dialkyl monomer such as diallyl dimethyl ammonium chloride, but preferably the cationic monomer is a dialkylaminoalkyl (meth)—acrylate or -acrylamide. Although the polymer can be in free base form, especially when it is a cationic acrylamide or methacrylamide, it is preferably in the form of an acid addition or quaternary ammonium salt.

When the monomer is a cationic acrylamide or methacrylamide, the dialkylaminoalkyl group is generally a dialkylamino propyl or dialkylamino isopropyl group. When the monomer is a cationic acrylate or methacrylate, the dialkylaminoalkyl group is generally a dialkylaminoethyl group.

It is usually preferred for the monomer to be a dialkylaminoalkyl meth acrylate acid addition or quaternary ammonium salt, most preferably dimethylaminoethyl methacrylate. Usually it is present as the methyl chloride quaternary ammonium salt.

If the polymer is to be water soluble, it is made in the absence of cross linking agent. Usually, however, the rheology of the composition is improved when the polymer is water swellable rather than water soluble, in which event the polymer is cross linked. The cross linking is generally achieved during polymerisation by including a polyethylenically unsaturated monomer in the monomer blend as cross linking agent. Any of the conventional polyethylenically unsaturated cross linking agents which are soluble in the monomer or monomer blend can be used, including materials which are di, tri or tetra ethylenically unsaturated such as methylene bis acrylamide.

The amount of cross linking agent is generally in the range from 10 to 10,000 parts by weight cross linking agent per million parts (by dry weight) of monomer, most preferably around 50 to 500 ppm.

The polymer is made by reverse phase emulsion polymerisation in a liquid phase provided by the liquid hydrophobic ester. Reverse phase polymerisation is frequently conducted instead in the presence of a mineral oil but this carries the mineral oil into the final composition. Since the compositions are generally used for cosmetic or pharmaceutical purposes, a liquid hydrophobic ester is often used as the continuous phase. It is possible to select esters which are cosmetically or pharmaceutically acceptable and which are sufficiently hydrophobic to be useful as the continuous phase in a reverse phase polymerisation.

The ester can be formed by reaction between a monocarboxylic acid or a di- or higher carboxylic acid with an alcohol (often $C_{6-12}$) or a polyol which may be a diol, triol or tetrol. The ester is usually aliphatic. When a polyol is used, usually all the hydroxy groups are esterified (usually with monocarboxylic acid) but in some instances the polyol may be only partially esterified. The esterifying groups may be the same or different. Generally they are aliphatic. The esterifying groups are preferably provided by aliphatic acids containing 5 to 16 carbon atoms, preferably 8 to 10 or 12 carbon atoms, such as caproic acid, caprylic acid and capric acid. Mixtures of esterifying groups may be used.

The liquid ester may be a naturally occurring material such as a vegetable oil or it may be a synthetically produced material. Preferred synthetically produced materials are esters of propylene glycol or butylene glycol, most preferably propylene glycol. A preferred liquid ester is the diester of propylene glycol with a mixture of caprate and caprylate groups. Another preferred ester is octyl cocoate, ie the ester obtained by reaction between octyl alcohol and the carboxylic acid derived from coconut oil.

The amount of the liquid ester is dictated primarily by the need to provide a satisfactory reverse phase emulsion medium and so is usually 0.5 to 2 parts by weight per part by weight of the cationic polymer (dry weight). Generally the amount is around 0.7 to 1.3 parts, most preferably about 1 part ester per part by weight polymer.

The polymer is made by conventional reverse phase emulsion procedures, namely by emulsifying 1 part by weight (dry weight) of the aqueous monomer into 0.5 to 2 parts by weight of the liquid ester in the presence of conventional surfactant and/or polymeric stabiliser additives so as to form a substantially stable emulsion. This is polymerised by addition of conventional initiator to form a reverse phase emulsion of aqueous polymer particles in the liquid ester. The amount of water is generally 0.5 to 2 parts, often around 0.7 to 1.3 parts, per part by weight (dry weight) of the polymer.

Although the water can be left in the polymer particles, its presence may make it more difficult to obtain a clear base composition and so preferably the water is distilled from the reverse phase emulsion by distillation under reduced pressure, so as to produce a substantially anhydrous reverse phase emulsion of the cationic polymer particles emulsified (i.e., stably dispersed) in the liquid ester.

A preferred anhydrous reverse phase emulsion of this type, for use in the invention, is available from Allied Colloids Inc. of Suffolk, Va. under the trade name Salcare SC96.

In order to utilise the viscosifying properties of the polymer, it is necessary to solvate the polymer particles substantially to the maximum extent that is possible. Since the particles are water soluble or water swellable, they could be solvated merely by the addition of sufficient water. For instance the amount of solvating liquid must usually be at least 10 times, and usually at least 20 times the weight of polymer and typically it is 30 to 100 or even 200 times the weight of polymer. However when the solvating liquid is water or when it contains a large amount of water, an opaque or cloudy composition is obtained because of the immiscibility of the water and the liquid ester. In the invention we find we can obtain a clear composition provided we use selected amounts of propylene glycol and/or butylene glycol in combination with an appropriate amount of glycerine.

Because of the high polarity of glycerine it might be thought that it would be a satisfactory solvating liquid. However we find that if glycerine is used by itself it does not adequately solvate the polymer.

Propylene glycol and/or butylene glycol will solvate the polymer but when used alone they give a cloudy composition, again presumably due to incompatibility between the solvating liquid and the liquid ester of the polyol. Also they can give a viscosity which is higher than desired and a rheology which is not entirely satisfactory. In the invention we find that we can obtain a composition having the desired viscosity and rheology characteristics and which is clear by selecting appropriately the combination of propylene and/or butylene glycol with glycerine.

When the solvating liquid consists only of propylene and/or butylene glycol with glycerine, the amount of propylene glycol and/or butylene glycol is usually at least 45% and generally at least 48%. However when other polyols are included in the solvating mixture these may replace some of the propylene and/or butylene glycol so that lower amounts, down to about 30%, usually at least about 35 or 40% and most preferably at least 44% of the propylene glycol and/or butylene glycol are satisfactory.

Suitable other polyols which can be used for this purpose include dipropylene glycol and/or tripropylene glycol, especially for use in combination with propylene glycol. These materials (di and tri propylene glycol) do not seem to be satisfactory for use in the absence of the propylene glycol. Other glycols or other polyols can be used, usually as relatively minor components in the solvating mixture provided they are cosmetically or pharmaceutically acceptable and do not significantly detract from the desirable clarity and gel properties of the compositions. Preferably the maximum amount of such other materials is not more than 30% and generally not more than 25%.

The amount of glycerine is usually at least 10% and often at least 11 or 12%. Usually it is not more than about 50% and in most compositions it is below about 45%.

The optimum for each of the components depends upon the choice of the liquid ester, the choice of the polymer and the amount of the liquid ester and the amount of the polymer. For instance, when the polymer and the liquid ester are each present in an amount of around 2% (i.e., about 4% by weight reverse phase emulsion) best results are obtained with around 53 to 83% propylene glycol and 43 to 12% glycerine, but when the amounts of polymer and liquid ester are halved (about 1% of each) best results are generally obtained with around 48 to 80% propylene glycol and 50 to 17% glycerine. Similarly, when using butylene glycol, at 2% polymer best results are achieved with around 62 to 86% butylene glycol and 32 to 11% glycerine, but at 1% polymer best results are achieved with around 60 to 82% butylene glycol and 13 to 38% glycerine.

As a generality, it will be found to be possible to obtain clear compositions by appropriate selection of the amount of the glycol and the glycerine (optionally with other polyol) by routine experimentation. Typically such routine experimentation would involve using around 65 to 75% propylene or butylene glycol with around 20 to 30% glycerine, for instance around 70% glycol and 25% glycerine, and to establish whether such a composition gives a clear gel. If it does not, then formulations should be tried with more glycol and less glycerine, and with less glycol and more glycerine, until a clear composition is found. Having established a clear composition, the proportions of glycol and glycerine can be varied to observe the optimum combination of clarity and viscosity. If desired, other polyol can be added at this stage to ascertain the effect of substituting some of the glycol with other polyol, or alternatively other polyol can be introduced in the initial formulation.

In each instance, the amounts of the components are selected such that the composition has a clarity of less than 30 NTU and preferably less than 20 NTU and most preferably less than 10 NTU when measured by a Hach turbidimeter. The clear composition may alternatively be described as translucent.

The protocol for measuring the clarity of the composition on a Hach turbidimeter is as follows, namely a Hach 2100 Turbidity Meter is calibrated using Gelex Secondary Standards. If the reading is not with ±5.0%, the Meter is re-calibrated using Formazin Standard. A clean sample cell is filled with the test composition to the required line and the cell is capped. The cell is placed in the cell compartment so the orientation mark on the cell aligns with the mark of the cell compartment and the lid is closed. The Meter is operated in the auto range mode and Signal Average is read. Each evaluation is carried out in triplicate.

The viscosity of the composition can be adjusted by varying the amounts of the solvating mixture, while maintaining clarity. One advantage of the invention is that it is possible to increase viscosity (by appropriate choice of solvating liquids) and thus it is possible to economise on the amount of polymer. The composition is generally formulated so that it has a viscosity of at least 20,000 cp (measured on a Brookfield LVT spindle F at the appropriate speed of rotation, for instance 1.5 rpm for very high values and 15 rpm for lower values). Often the viscosity is at least 30,000 cp and in many compositions it is above 100,000, for instance 200,000 up to 600,000 cp or in some instances up to 900,000 cp.

The composition which is made in accordance with the invention may consist only of the polymer, the liquid hydrophobic ester together with very small amounts (for instance less than 0.05 parts per part by weight polymer) of emulsifier, and stabiliser, together with the solvating mixture. Thus the amount of the solvating mixture is then in the range 90 to 99% so as to provide 100% of the composition. Often the amount of polymer and ester are each 0.5 to 2.5%, in which event the amount of solvating mixture is then 95 to 99%.

The base composition is preferably formulated initially so as to consist only of the polymer, liquid ester and polyol mixture and this base composition is then used as a carrier for desirable cosmetic or pharmaceutical active ingredients, and other optional ingredients, so as to provide a cosmetic or pharmaceutical composition. Preferably this final composition is also clear. Alternatively such components can be included in the composition during its initial manufacture. The amount of such components is usually in the range 0.1 to 20% by weight of the composition, preferably 0.1 to 10%.

Cosmetic compositions generally include a fragrance. Other materials that can be included in cosmetic composition include skin conditioning agents such as acetylated lanolin alcohol, allantion, aloe vera, acetamide monoethanolamine, dimethicone copolyol, dimethyl polysiloxane, hair conditioning agents such as, amodimethicone, cyclomethicone, panthenol, lauramide diethanolamine, lauramine oxide, silk protein, antioxidants such as butylated hydroxyanisol, hydroquinone, alpha hydroxy acids such as lactic acid, citric acid, preservatives such as propyl paraben, imidazolidinyl urea, and sun screening agents such as para amino benzoic acid, octyl salicylate, and octyl methoxycinnamate.

The compositions are generally substantially anhydrous but if desired water can be included in the compositions provided it does not seriously detract from clarity and other desirable properties of the compositions.

The anhydrous compositions can be formulated so as to be exothermic when wetted on the body. In a second aspect of the invention we provide a composition which is exothermic when applied to the human body and which is anhydrous and contains a polymeric thickener (preferably as described above) and one or more glycols and/or glycerin (preferably as described above). The composition can be opaque, clear or cloudy. Such a composition liberates heat when exposed to humidity.

The following are examples and show the ingredients which are blended, and the properties of the resultant blend. All amounts are % by weight.

In each instance the polymer emulsion is the substantially anhydrous reverse phase emulsion of lightly cross linked homopolymer of dimethylaminoethyl methacrylate methyl chloride polymer in propylene glycol caproate caprylate ester containing substantially equal amounts by weight of polymer and ester and which is available under the tradename Salcare SC96. The amount of emulsion is quoted and half of this amount is polymer and half is ester. Thus 4% polymer emulsion indicates 2% polymer and 2% of the liquid ester.

In each example the composition is made by blending the listed components other than the emulsion until smooth and homogeneous, and the emulsion is then added with moderate agitation being continued until the mix is again smooth and homogeneous.

Fragrance and/or other active ingredient can be included as desired.

EXAMPLE 1

|  | 1A | 1B | 1C | 1D |
|---|---|---|---|---|
| Propylene Glycol | 85 | 83 | 74 | 63 |
| Glycerin | 10.6 | 12.6 | 21.6 | 32.6 |
| Germaben II | 0.4 | 0.4 | 0.4 | 0.4 |
| Emulsion | 4 | 4 | 4 | 4 |
| Viscosity cP | 630,630 | 466,128 | 270,894 | 513,368 |
| Turbidity Reading (NTU) | 42.3 | 30.1 | 14.6 | 6.46 |
| Comments | cloudy | clear | clear | clear |

EXAMPLE 2

|  | Formulations | | |
|---|---|---|---|
| Cloudy | 2A | 2B | 2C |
| Propylene Glycol | 82 | 73 | 65 |
| Glycerin | 15.6 | 24.6 | 32.6 |
| Germaben II | 0.4 | 0.4 | 0.4 |
| Emulsion | 2 | 2 | 2 |
| Viscosity cP | 32,195 | 37,674 | 61,074 |
| Turbidity Reading | 32.1 | 15 | 10.5 |
| Comments | cloudy | clear | clear |

EXAMPLE 3

| Component | 3A Concentration | 3B Concentration | 3C Concentration |
|---|---|---|---|
| Butylene Glycol | 64 | 77 | 84 |
| Glycerin | 31.6 | 18.6 | 11.6 |
| Germaben II | 0.4 | 0.4 | 0.4 |
| Emulsion | 4 | 4 | 4 |
| Viscosity cP | 559,884 | 248,040 | 442,104 |
| Turbidity Reading | 25.2 | 13.1 | 17.8 |
| Comments | clear | clear | clear |

EXAMPLE 4

| Component | 4A Concentration | 4B Concentration | 4C Concentration |
|---|---|---|---|
| Propylene Glycol | 27.5 | 46.5 | 47.5 |
| Dipropylene Glycol | 41.5 | 22.5 | 21.5 |
| Glycerin | 26.6 | 26.6 | 26.6 |
| Germaben II | 0.4 | 0.4 | 0.4 |
| Emulsion | 408,096 | 4 | 383,760 |
| Viscosity Reading (NTU) | 28.7 | 292,188 | 18.5 |
| Comments | clear | clear | clear |

EXAMPLE 5

| Component | 5A | 5B | 5C | 5D |
|---|---|---|---|---|
| Propylene Glycol | 34.5 | 44.5 | 48.5 | 53.5 |
| Tripropylene Glycol | 34.5 | 24.5 | 20.5 | 15.5 |
| Glycerin | 26.6 | 26.6 | 26.6 | 26.6 |
| Germaben II | 0.4 | 0.4 | 0.4 | 0.4 |
| Emulsion | 4 | 4 | 4 | 4 |
| Viscosity cP | 105,456 | 176,280 | 223,470 | 244,062 |
| Turbidity Reading | 140 | 26.1 | 19.2 | 12.5 |
| Comments | cloudy | clear | clear | clear |

EXAMPLE 6

An exothermic, clear, gelled, hair conditioner formulation is made by blending 4% by weight of the anhydrous polymer emulsion Salcare SC96 with 24.6% by weight glycerine, 70% by weight propylene glycol and 1.4% by weight hair conditioner additives (dye, fragrance and vegetable extract Cayenne extract). The product was a substantially clear gel having a viscosity (Brookfield LVT spindle F at 15 rpm) of about 350,000 cps and pH at room temperature of about 4.7.

We claim:

1. A clear gelled composition comprising
   (a) 0.5 to 5% by weight of the overall composition of a water soluble or water swellable cationic polymer formed from water soluble ethylenically unsaturated monomer or monomer blend
   (b) 0.5 to 5% by weight of the overall composition of a hydrophobic ester wherein the amount of the ester of is 0.5 to 2 parts per part by weight of the cationic polymer and the ester is a liquid which is substantially non-solvating for the polymer throughout the range 15 to 100° C., and
   (c) 80 to 99% by weight of the overall composition of a polyol mixture which solvates the polymer into a gel and which comprises
      (c1) 30 to 88% by weight of the polyol mixture of propylene glycol and/or butylene glycol
      (c2) 8 to 55% by weight of the polyol mixture of glycerine and
      (c3) 0 to 35% by weight of the polyol mixture of other polyol and
   wherein the amounts of the components of the polyol mixture are selected such that the composition has a clarity of below 30 NTU.

2. A composition according to claim 1 which has been made by blending a substantially anhydrous reverse phase emulsion of the polymer in the liquid ester with the polyol mixture.

3. A composition according to claim 1 in which the polymer is a cross linked water swellable polymer of dialkylaminoalkyl (meth) -acrylate or -acrylamide.

4. A composition according to claim 1 in which the polymer is a cross linked water swellable homopolymer of dimethylaminoethyl methacrylate methyl chloride quaternary salt.

5. A composition according to claim 1 in which the liquid ester is the diester of propylene glycol with caprate and caprylate mixed groups.

6. A composition according to claim 1 in which the polyol mixture contains 12 to 50% glycerine by weight of the overall composition and 45 to 88% by weight of the overall composition propylene glycol and/or butylene glycol.

7. A composition according to claim 1 in which the polyol mixture consists essentially of 48 to 83% by weight of the overall composition propylene glycol and 50 to 12% by weight of the overall composition glycerine.

8. A composition according to claim 1 in which the polyol mixture consists essentially of 62 to 86% by weight of the overall composition butylene glycol and 32 to 12% by weight of the overall composition glycerine.

9. A cosmetic or pharmaceutical composition comprising a gelled composition according to any preceding claim into which optional additives and active ingredients selected from fragrances, pharmaceutically active and cosmetically active ingredients have been incorporated in an amount of up to 20% by weight of the overall composition.

10. A composition which is exothermic when exposed to moisture and which is an anhydrous gelled mixture of a water soluble or water swellable synthetic cationic polymeric thickener and one or more glycols and/or glycerine.

* * * * *